Figure 1:
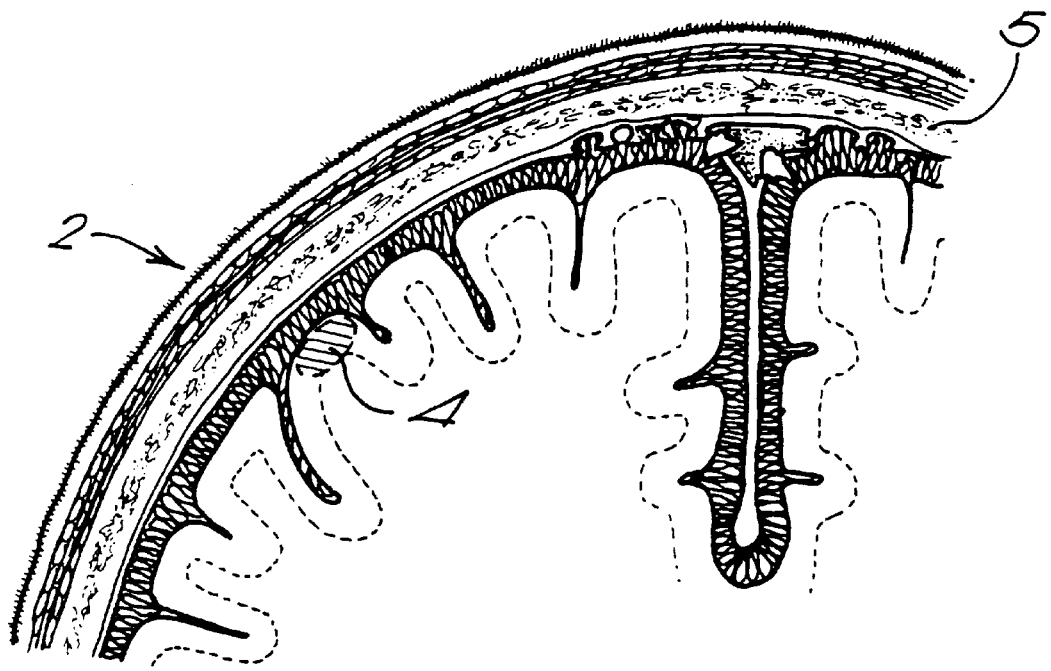

United States Patent [19]
Evans

[11] Patent Number: 5,951,481
[45] Date of Patent: Sep. 14, 1999

[54] APPARATUS AND METHOD FOR NON-INVASIVE MEASUREMENT OF A SUBSTANCE

[75] Inventor: Peter Dilwyn Evans, Wales, United Kingdom

[73] Assignee: Critikon Company, L.L.C., Tampa, Fla.

[21] Appl. No.: 08/933,520

[22] Filed: Sep. 18, 1997

[30] Foreign Application Priority Data

Sep. 20, 1996 [GB] United Kingdom ............... 9619693

[51] Int. Cl.⁶ ............................................ A61B 5/10
[52] U.S. Cl. .................... 600/473; 600/437; 73/653; 356/351
[58] Field of Search .................. 600/407, 473, 600/476, 437, 438, 475, 453, 552; 356/351; 73/657

[56] References Cited

U.S. PATENT DOCUMENTS

| | | | |
|---|---|---|---|
| 4,223,680 | 9/1980 | Jobsis . | |
| 4,339,954 | 7/1982 | Anson et al. | 73/657 |
| 4,834,111 | 5/1989 | Khanna et al. | 73/657 |
| 4,966,459 | 10/1990 | Monchalin | 73/657 |
| 5,007,428 | 4/1991 | Watmough | 600/473 |
| 5,174,298 | 12/1992 | Dolfi et al. | 600/476 |
| 5,212,667 | 5/1993 | Tomlinson, Jr. et al. . | |
| 5,451,785 | 9/1995 | Faris | 600/473 |
| 5,596,987 | 1/1997 | Chance | 600/310 |

FOREIGN PATENT DOCUMENTS

| | | |
|---|---|---|
| 41 28 744 | 4/1993 | Germany . |
| WO 89 00278 | 12/1989 | WIPO . |
| WO 94 28795 | 12/1994 | WIPO . |

*Primary Examiner*—Brian L. Casler
*Attorney, Agent, or Firm*—Larry L. Saret; Laff, Whitesel, Conte & Saret, Ltd.

[57] ABSTRACT

An apparatus and method of non-invasive measurement of a chosen region (4) within a body (2), using the transmission of an ultrasonic pulse and the measurement of back scattered optical radiation which has been modulated by the ultrasonic pulse at the region of interest. There may be two or more ultrasonic transmitters (10, 14) to allow control of the vibration of the ultrasonic pulses at the region (4) of interest.

4 Claims, 2 Drawing Sheets

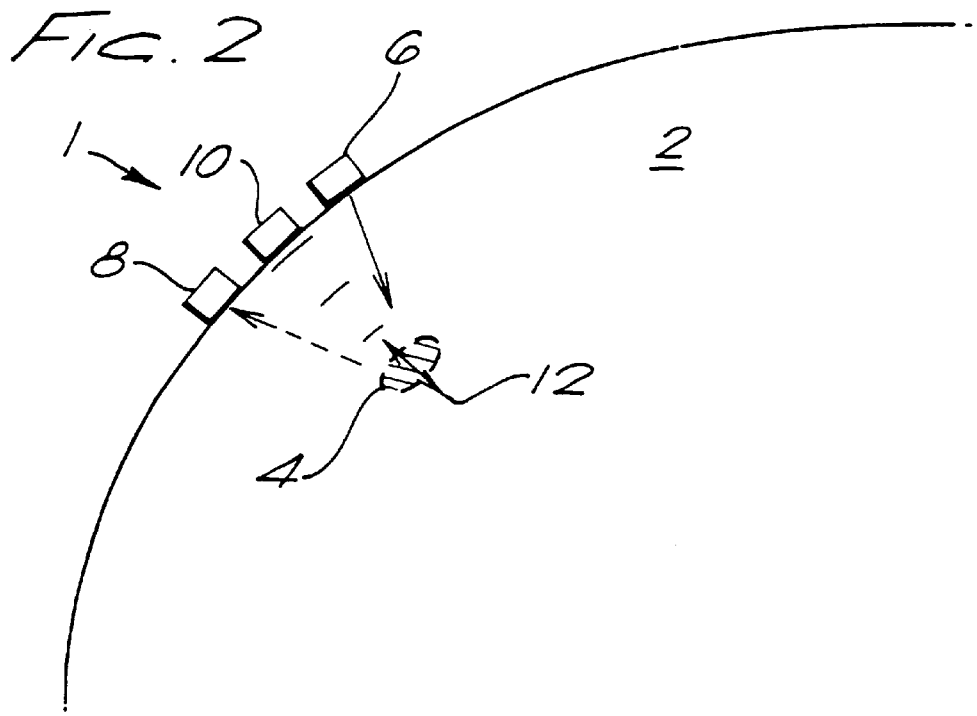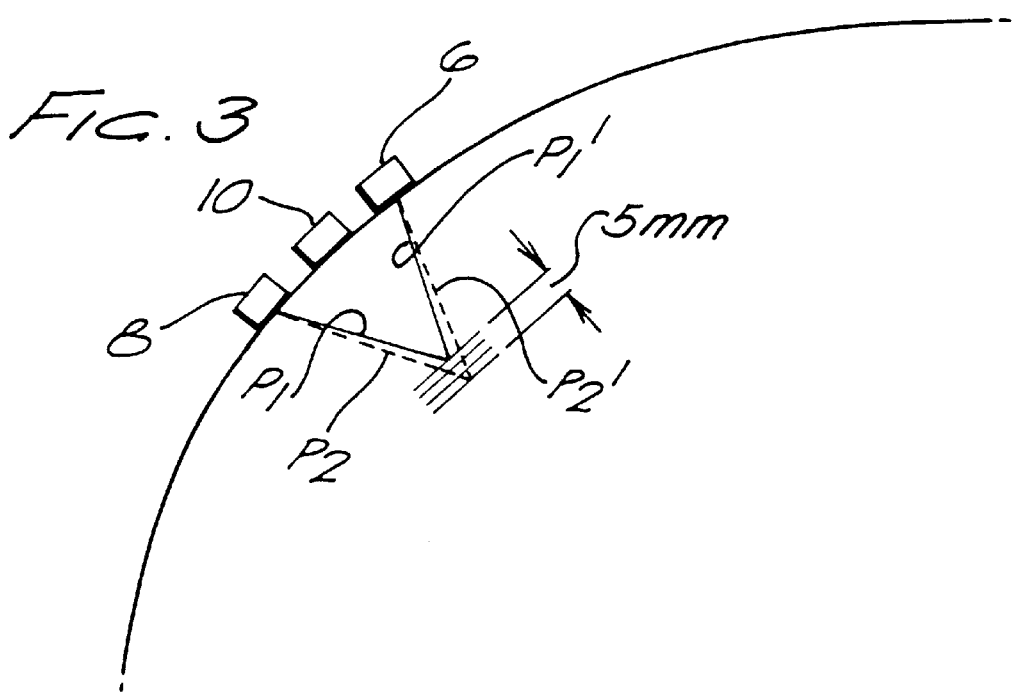

APPARATUS AND METHOD FOR NON-INVASIVE MEASUREMENT OF A SUBSTANCE

This invention relates to an apparatus and method for non-invasive measurement of a substance, particularly measurement of a substance in a chosen region within a part of the human body, for example, the head. The apparatus and method could equally be applied to other situations in which characteristics of a substance in chosen region within a sample are required to be measured.

Methods of non-invasive measurement of characteristics of a substance using radiation of near infrared wavelengths are well known. The characteristics of a substance can be determined by studying the back scattered radiation received at a detector. An example of such a non-invasive measurement technique is given in U.S. No. 5,419,321 in which an emitter is placed against the tissue in which the substance to be measured is found and two detectors are spaced from the emitter to detect radiation which is being scattered and attenuated by the skin, tissue or organ of the patient.

Such known non-invasive measurement techniques have the disadvantage of the detectors receiving a lot of back scattered radiation from skin and tissue other than the tissue of interest.

Another field of non-invasive monitoring is that of non-invasive light imaging of breast tumours in which light is transmitted through the tissue and an image is produced.

It is been recognised in this field that it is a benefit to identify light travelling through a particular region of the tissue in order that this light can be recognised by the detector and an image built up region by region.

It has been found that an ultrasonic pulse can be directed to a particular region to coincide with the light being transmitted through that region. The ultrasonic pulse "tags" the light by modulating the light passing through the ultrasonic pulse.

The ultrasonic modulation of light imaging is described in "A comprehensive approach to breast cancer detection using light: photon localisation by ultrasound modulation and tissue characterisation by spectral discrimination" by F. A. Marks et al pages 500 to 510 of SPIE Vol. 1888, 1993, WO89/00278, U.S. No. 5212667 and "Ultrasound-modulated optical tomography for thick tissue imaging" by L Wang et al pages 237 to 348, SPIE Vol. 2626, 1995.

According to a first aspect of the present invention, there is provided an apparatus for non-invasive measurement of a substance comprising an ultrasound transmitter, an electromagnetic radiation emitter and an electromagnetic radiation detector all arranged to be disposed on the surface of a body in which a region of which the substance is to be measured may be found, wherein the ultrasound transmitter directs a pulse of ultrasound of predetermined duration into the body, the electromagnetic radiation emitter emits radiation towards the region and back scattered radiation is detected by the electromagnetic radiation detector, the apparatus further comprising analyzing means for analyzing the back scattered radiation to distinguish light which has been scattered from the region and to determine the characteristics of the substance at the region.

Preferably, the electromagnetic radiation is near infrared radiation.

There may be two or more ultrasound transducers directed towards the region of interest. The ultrasound transducers may be phased in order to vary the direction of the ultrasonic vibration at the region of interest.

The electromagnetic radiation emitter and detector may be disposed at the same point on the surface of the body. Alternatively, the electromagnetic radiation emitter and detector may be spaced apart on the surface of the body.

The apparatus may be arranged to detect electromagnetic radiation at a time calculated as the time which the ultrasonic pulse detection reaches the region of interest. A further detection of electromagnetic radiation may take place after a delay.

According to a second aspect of the present invention there is provided a method of non-invasive measurement of a substance comprising the steps of transmitting a pulse of ultrasonic signal towards a region of interest within a body, the pulse of the ultrasonic signal being calculated to determine the size of the region which will be modulated by the ultrasonic signal, emitting electromagnetic radiation after a delay determined by the distance between the region of interest and the source of the ultrasonic pulse, emitting a second emission of electromagnetic radiation after a delay, detecting the back scattered electromagnetic radiation, analyzing the back scattered electromagnetic radiation which has been modulated by the ultrasonic pulse and determining a characteristic of the substance if present in the region of interest.

Preferably, the electromagnetic radiation is near infrared radiation at a given number of wavelengths for determining the required characteristics of the substance in the region of interest.

Preferably, the electromagnetic radiation detected by the detector is used to calculate the concentration of the substance by the use of the Beer Lambert Law.

The electromagnetic radiation may be pulsed to increase its intensity.

Figure 4:
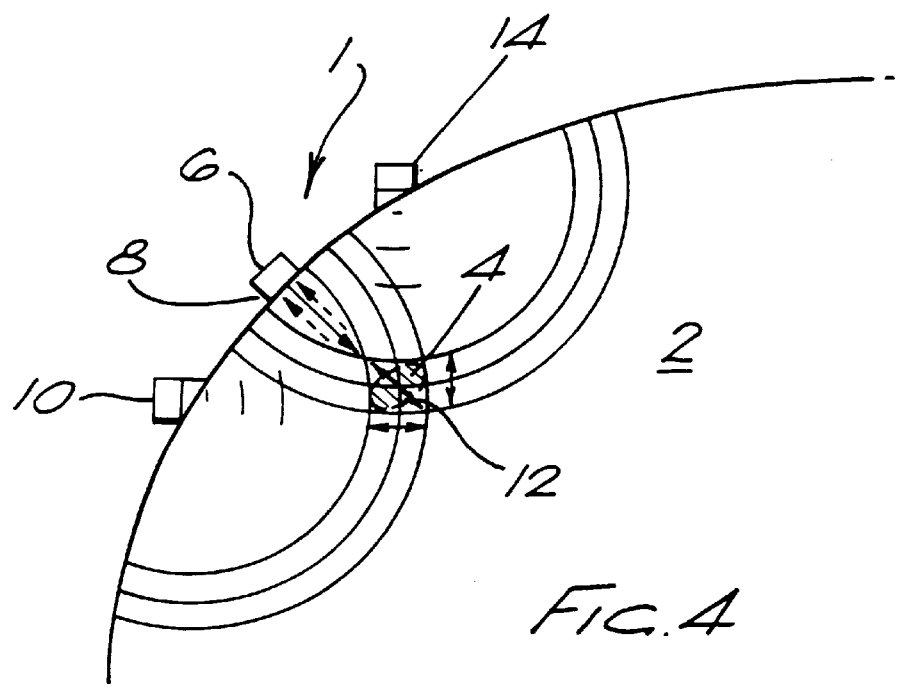

Embodiments of the present invention are now described with reference to the accompanying drawings in which:

FIG. 1 coronal section showing an example of a region to be monitored;

FIG. 2 section of a body showing the operation of the first embodiment of the present invention;

FIG. 3 is a section of a body showing the path lengths of light of the first embodiment of the present invention; and FIG. 4 is a section of a body showing the operation of a second embodiment of the present invention.

Referring to the drawings, an apparatus and method of non-invasive measurement of a chosen region within a body is described. FIG. 1 shows a coronal section illustrating a region 4 within the tissue of a body 2 to be monitored. Known methods of near infrared spectroscopy which determine characteristics of the substance due to the intensity of the infrared radiation back scattered from the substance have the disadvantage that the back scattered radiation contains a large amount of background radiation which has been scattered from tissue which is not being monitored. In the example of the coronal section, back scattered information which is not required is received from the extracerebral tissues 5.

As shown in FIG. 2, a system 1 is provided in which an ultrasound transmitter 10 transmits a short pulse of high frequency ultrasonic signal into the body 2. The duration of the pulse of the ultrasonic signal is determined by the size of the region 4 to be monitored. In the example of the cerebral cortex illustrated in FIG. 1, a region of approximately 5 mm depth has been chosen. The speed of sound in cerebral tissues is close to the speed of sound in water and is approximately 1500 metres per second. Therefore a pulse of approximately 3 $\mu$sec is required for the 5 mm depth of the region.

Similarly, the depth travelled by the ultrasonic pulse into the body can be determined. After a delay of approximately 13 μsec from the emission of the ultrasonic pulse, the pulse has travelled approximately 20 mm into the body.

An electromagnetic radiation source 6 in the form of a gated laser source is provided on the surface of the body 2. A signal of near infrared wavelength is directed towards the chosen region 4. The signal may contain more than one wavelength of light.

An optical detector 8 is also provided on the surface of the body 2 and receives back scattered electromagnetic radiation which has originated at the gated laser source 6.

Specific wavelengths of radiation can be chosen to be emitted into the body 2 to determine particular qualities of the chosen region 4.

A delay of time from the transmission of the ultrasonic pulse is allowed for the ultrasound pressure waves to travel to the region 4 of interest. After the delay, the optical signal detected at the detector 8 is measured. The optical signal which has been scattered by the region 4 of interest through which the ultrasound pressure waves have been travelling, is modulated. The modulation may take the form of a change in the frequency, amplitude or speckle characteristics of the optical signal. The modulated optical signal is separated from the other optical signals received.

A further delay of time is allowed, after which another measurement at the detector 8 of the magnitude of the modulated optical signal is taken. The difference between these two measurements is related to the quantity of a substance of interest within the indicated region 4 of the body 2. The path lengths P1, P2 of the optical signals is defined by the delay between the two pulses, thus allowing the calculation of the concentration of the substance in the region 4 of interest by the use of Beer Lambert Law. FIG. 3 shows the path lengths P1, P2 travelled by the two modulated optical signals.

The reason the optical signal is modulated as it passes through the ultrasonic pulse could be due to one of a number of reasons including a change in refractive index of the tissue, change in density of the tissue, a Doppler shift caused by the ultrasonic pulse or phase variation. (See the discussion in SPIE Vol. 2626, 1995).

A pulsed optical source 6 can be used to increase the intensity of light emitted into the body 2.

A An alternative embodiment of the present invention is shown in FIG. 4 in which two ultrasound transmitters 10, 14 are used. In this embodiment the optical emitter 6 and detector 8 are combined. The optical emitter/detector 6,8 is position between the two ultrasound transmitters 10, 14.

As shown in FIG. 4, the ultrasound transmitters 10, 14 transmit pulses which radiate from the transmitters 10, 14 into the body 2. The pulses transmitted from the two ultrasonic transmitters 10, 14 coincide at the region 4 of interest a predetermined time from transmission. At this predetermined time, the optical signal is detected at detector 8.

The two ultrasound transmitters 10, 14 can be in the same phase in which case the combined ultrasonic pulse will vibrate in the direction of the optical signal. If the ultrasound transmitters 10, 14 are out of phase, a vibration in the region of interest is obtained perpendicular to the direction of the optical signal.

The use of two or more ultrasound transmitters 10, 14 increases the control over the vibrations at the region 4 of interest.

Modifications and improvements can be made to the foregoing without departing from the scope of the present invention.

I claim:

1. A method of non-invasive measurement of a substance comprising the steps of transmitting a pulse of ultrasonic energy towards a region of interest within a body, the pulse of the ultrasonic energy being calculated to determine a size of the region which will be modulated by the ultrasonic energy, emitting electromagnetic radiation after a delay determined by a distance separating the region of interest and the source of the ultrasonic energy pulse, emitting a second emission of electromagnetic radiation after a delay, detecting back scattered electromagnetic radiation, analyzing the back scattered electromagnetic radiation which has been modulated by the ultrasonic energy pulse, determining a characteristic of the substance if present in the region of interest.

2. A method as claimed in claim 1, wherein the electromagnetic radiation is near infrared radiation at the given number of wavelengths for determining characteristics of the region of interest.

3. A method as claimed in claim 1, wherein the electromagnetic radiation detected is used to calculate a concentration of substance by the use of the Beer Lambert Law.

4. A method as claimed in claim 1 wherein the electromagnetic radiation is pulsed to increase its intensity.

* * * * *